(12) United States Patent
Agano

(10) Patent No.: US 6,816,160 B2
(45) Date of Patent: Nov. 9, 2004

(54) IMAGE DATA COMPUTING APPARATUS

(75) Inventor: Toshitaka Agano, Minami-Ashigara (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 262 days.

(21) Appl. No.: 10/013,526

(22) Filed: Dec. 13, 2001

(65) Prior Publication Data

US 2002/0118179 A1 Aug. 29, 2002

(30) Foreign Application Priority Data

Dec. 20, 2000 (JP) ........................................ 2000-387114

(51) Int. Cl.[7] .............................................. G06T 15/00
(52) U.S. Cl. ........................... 345/419; 367/7; 600/437; 600/459
(58) Field of Search ............................. 367/7; 345/419; 600/437–448, 459

(56) References Cited

U.S. PATENT DOCUMENTS 4,694,434 A * 9/1987 von Ramm et al. ............ 367/7

OTHER PUBLICATIONS

Motizuki, Tsuyoshi, "A Principle of Three–Dimensional Display", Clinical Radiation, vol. 43, No. 11, 1998, pp. 1281–1283.

* cited by examiner

Primary Examiner—Mark Zimmerman
Assistant Examiner—Adam Arnold
(74) Attorney, Agent, or Firm—Sughrue Mion, PLLC

(57) ABSTRACT

An image data computing apparatus for computing three-dimensional image data on the basis of detection data obtained by employing a two-dimensional sensor array including a plurality of ultrasonic sensors. The apparatus includes a line memory for storing the detection data obtained on the basis of output signals of the plurality of sensors, a storage unit for storing as a table therein transfer time period data determined by the relations between distances from a transmission unit to the respective sensors through respective points to be measured and transfer velocities of the ultrasonic wave in the corresponding paths, and a computation unit for reading the detection data stored in the line memory in accordance with the transfer time period data and computing image data at the respective points to be measured on the basis of the read detection data.

20 Claims, 12 Drawing Sheets

FIG.7

| | $y_1$ | $y_2$ | ... | $y_n$ | ... | $y_L$ |
|---|---|---|---|---|---|---|
| $x_1$ | $t(x_1, y_1)$ | $t(x_1, y_2)$ | | $t(x_1, y_n)$ | | $t(x_1, y_L)$ |
| $x_2$ | $t(x_2, y_1)$ | $t(x_2, y_2)$ | | $t(x_2, y_n)$ | | $t(x_2, y_L)$ |
| ... | | | | | | |
| $x_m$ | $t(x_m, y_1)$ | $t(x_m, y_2)$ | | $t(x_m, y_n)$ | | $t(x_m, y_L)$ |
| ... | | | | | | |
| $x_P$ | $t(x_P, y_1)$ | $t(x_P, y_2)$ | | $t(x_P, y_n)$ | | $t(x_P, y_L)$ |

L SENSOR POSITIONS

P POINTS TO BE MEASURED (P=q×r×s)

FIG.9

| | $y_1$ | $y_2$ | ..... | $y_n$ | ..... | $y_L$ |
|---|---|---|---|---|---|---|
| $x_1$ | $t(x_1, y_1)$ $w(x_1, y_1)$ | $t(x_1, y_2)$ $w(x_1, y_2)$ | | $t(x_1, y_n)$ $w(x_1, y_n)$ | | $t(x_1, y_L)$ $w(x_1, y_L)$ |
| $x_2$ | $t(x_2, y_1)$ $w(x_2, y_1)$ | $t(x_2, y_2)$ $w(x_2, y_2)$ | | $t(x_2, y_n)$ $w(x_2, y_n)$ | | $t(x_2, y_L)$ $w(x_2, y_L)$ |
| ...... | | | | | | |
| $x_m$ | $t(x_m, y_1)$ $w(x_m, y_1)$ | $t(x_m, y_2)$ $w(x_m, y_2)$ | | $t(x_m, y_n)$ $w(x_m, y_n)$ | | $t(x_m, y_L)$ $w(x_m, y_L)$ |
| ...... | | | | | | |
| $x_P$ | $t(x_P, y_1)$ $w(x_P, y_1)$ | $t(x_P, y_2)$ $w(x_P, y_2)$ | | $t(x_P, y_n)$ $w(x_P, y_n)$ | | $t(x_P, y_L)$ $w(x_P, y_L)$ |

L SENSOR POSITIONS

P POINTS TO BE MEASURED (P = q × r × s)

IMAGE DATA COMPUTING APPARATUS

BACKGROUND OF THE INVENTION

1. Field of the Invention

The present invention relates to an image data computing apparatus for computing three-dimensional image data on the basis of a plurality of two-dimensional image data acquired at different times, in order to make an ultrasonic diagnosis or the like.

2. Description of a Related Art

Heretofore, in order to obtain a three-dimensional image in an ultrasonic diagnosis or the like, it has been composited by acquiring a plurality of two-dimensional sectional images. Each of the two-dimensional sectional images is obtained by compositing a plurality of pixel data acquired in time series while a one-dimensional sensor array with a position sensor is kept scanning an object to be inspected. Further, the three-dimensional data is obtained by interpolating sections on the basis of the plurality of two-dimensional sectional images.

With this technique, however, time lags are involved in the scanning direction of the sensor array, so that the sectional images at different times are composited. Besides, the positions of the sensor are monitored, and the images are composited on the basis of the positional information, so that the composite image becomes obscure. Accordingly, the technique is not suitable for the image composition in which an organism is handled as the object to be inspected as in the ultrasonic diagnosis.

In order to solve the above problems, a two-dimensional sensor array should desirably be employed for the obtainment of a three-dimensional image. Considered by way of example is a method wherein an ultrasonic signal is acquired as the two-dimensional image of light by employing an optical fiber array. With this method, a plurality of ultrasonic images can be acquired at some time points on the basis of ultrasonic signals which enter the two-dimensional sensor array after the lapse of predetermined time periods from the transmission of a certain ultrasonic wave. The resulting two-dimensional data, however, are the mixed data of all the ultrasonic signals entering after the predetermined time periods have lapsed from the transmission and do not directly express data at a specified point on three dimensions.

Meanwhile, proceedings "Rinshoo-Hooshasen (Clinical Radiation)" Vol. 43 No. 11 (published in 1998 by Kanehara & Co., Ltd. in Tokyo) contains a report "A Principle of Three-Dimensional Display" written by Tsuyoshi Mochizuki. It is stated in the report that a conventional data collection method wherein an ultrasonic scanning section is successively moved requires a long time till the acquisition of the whole set of data, so it cannot obtain an accurate image in case of handling a moving object. As one solution to the drawback, a data collection method which employs a movable array vibrator of two dimensions is mentioned, and a method which displays the surface and internal information items of an object at the same time is introduced as a direct method. It is also stated, however, that hardware and signal processing inevitably become large scales in the present circumstances.

SUMMARY OF THE INVENTION

The present invention has been made in view of the problems as explained above. An object of the present invention is to provide an image data computing apparatus which computes three-dimensional image data on the basis of a plurality of two-dimensional image data acquired at different times by employing a two-dimensional sensor array.

In order to accomplish the object, an image data computing apparatus according to the first aspect of the present invention is an apparatus for computing three-dimensional image data on the basis of detection data obtained by transmitting an ultrasonic wave from transmission means toward points to be measured, which exist in a three-dimensional space, and detecting the ultrasonic wave reflected from the points to be measured by use of a two-dimensional sensor array including a plurality of sensors, and comprises: a line memory having a plurality of lines for storing the detection data obtained on the basis of output signals of said plurality of sensors respectively for a predetermined time period; storage means for storing as a table therein transfer time period data determined by relations between distances from the transmission means to the respective sensors through the respective points to be measured and transfer velocities of the ultrasonic wave in corresponding paths; and computation means for reading the detection data stored in said line memory in accordance with the transfer time period data stored in said storage means for the respective points to be measured, and for computing image data at the respective points to be measured on the basis of the read detection data.

Besides, an image data computing apparatus according to the second aspect of the present invention is an apparatus for computing three-dimensional image data on the basis of detection data obtained by transmitting an ultrasonic wave from transmission means toward points to be measured, which exist in a three-dimensional space, and detecting the ultrasonic wave reflected from the points to be measured by use of a two-dimensional sensor array including a plurality of sensors, and comprises: a line memory having a plurality of lines for storing the detection data obtained on the basis of output signals of said plurality of sensors respectively for a predetermined time period; storage means for storing as a table therein transfer time period data determined by relations between distances from the transmission means to the respective sensors through the respective points to be measured and transfer velocities of the ultrasonic wave in corresponding paths, and weighting factors for the detection data; and computation means for reading the detection data stored in said line memory in accordance with the transfer time period data stored in said storage means for the respective points to be measured, and for computing image data at the respective points to be measured by adding the read detection data after multiplying them by the weighting factors stored in said storage means for the respective points to be measured.

According to the present invention, three-dimensional image data can be computed on the basis of a plurality of two-dimensional image data acquired at identical sensor positions at different times by employing a two-dimensional sensor array. Accordingly, a clear three-dimensional image can be obtained even in an ultrasonic diagnostic apparatus which is directed toward organisms.

BRIEF DESCRIPTION OF THE DRAWINGS

FIG. 7 is a diagram showing a table which is used in the image data computing apparatus according to the first embodiment of the present invention;

FIG. 9 is a diagram showing a table which is used in an image data computing apparatus according to the second embodiment of the present invention;

DESCRIPTION OF THE PREFERRED EMBODIMENTS

Figure 1:
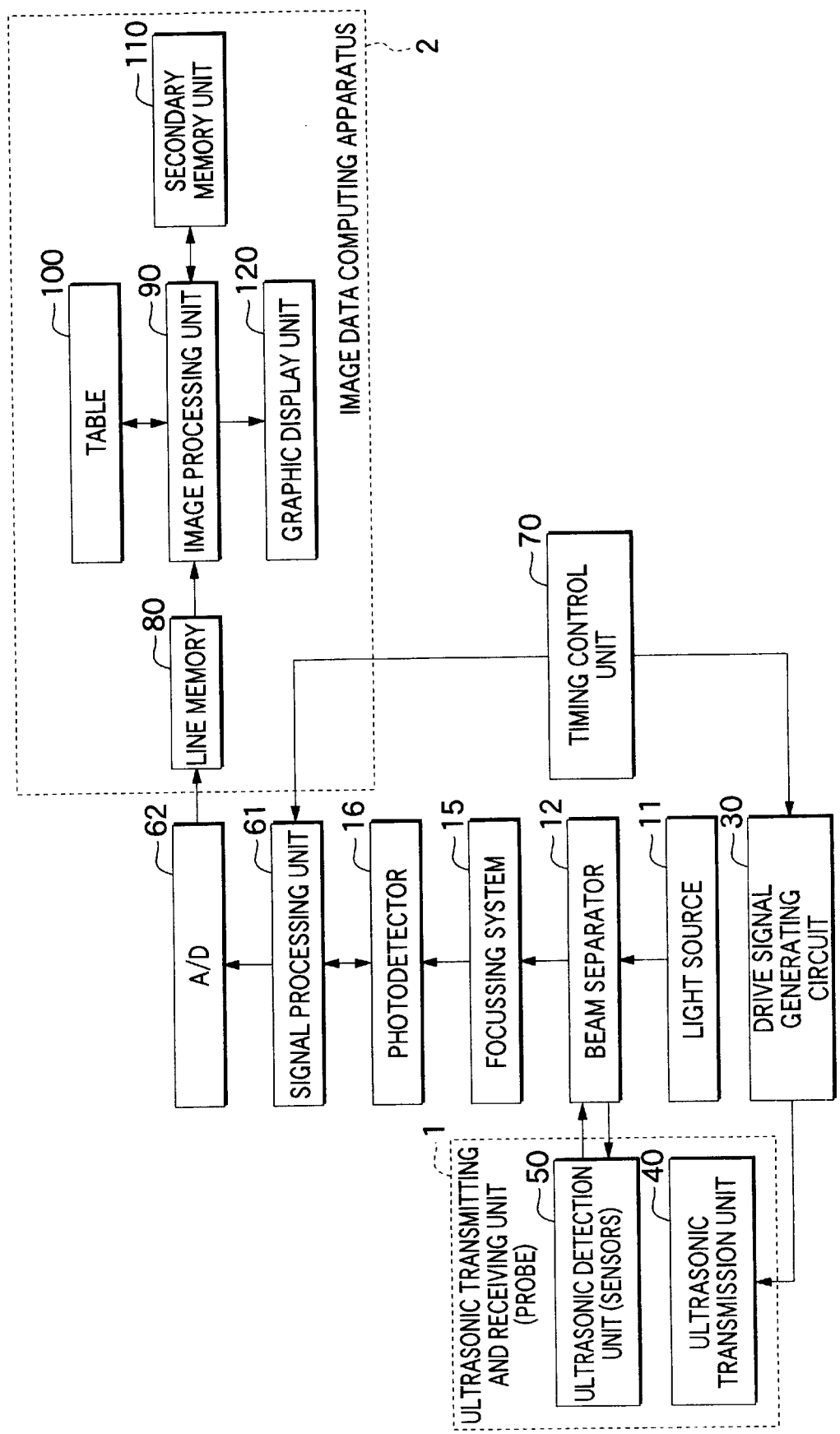
FIG. 1 is a block diagram showing an ultrasonic diagnostic apparatus which includes an image data computing apparatus according to the first embodiment of the present invention.

Now, embodiments of the present invention will be described in detail with reference to the drawings. Incidentally, the same reference numerals and signs will be assigned to the same constituents, which shall not be repeatedly explained.

FIG. 1 shows an ultrasonic diagnostic apparatus which includes an image data computing apparatus according to the first embodiment of the present invention. As shown in FIG. 1, the ultrasonic diagnostic apparatus includes a drive signal generating circuit 30 for generating a drive signal, and an ultrasonic transmission unit 40 for transmitting an ultrasonic wave on the basis of the drive signal. The ultrasonic transmission unit 40 is constructed by a vibrator which employs a piezoelectric device made of, for example, piezoelectric ceramics typified by PZT (Pb (lead) zirconate titanate) or a piezoelectric high polymer typified by PVDF (polyvinyl difluoride). The ultrasonic wave transmitted toward a diagnostic object is reflected from the diagnostic object, and is received by an ultrasonic detection unit 50. The ultrasonic detection unit 50 includes, for example, an optical fiber array and ultrasonic detecting elements. The ultrasonic transmission unit 40 and the ultrasonic detection unit 50 constitute an ultrasonic transmitting and receiving unit (probe) 1.

Besides, the ultrasonic diagnostic apparatus includes a light source 11, a beam separator 12, a focussing system 15 and a photodetector 16. A detection signal output from the photodetector 16 is subjected to signal processing in a signal processing unit 61, and is further converted into detection data in an A/D converter 62.

The detection data output from the A/D converter 62 is input to the image data computing apparatus 2, and is stored in a line memory 80. Also, transfer time period data for use in computing image data are stored as a table 100 in storage means such as a memory or a recording device. An image processing unit 90 constructs three-dimensional image data by computing the image data on the basis of the detection data stored in the line memory 80, with reference to the table 100. The image processing unit 90 further subjects the constructed three-dimensional image data to such processes as an interpolation process, a response modulation process and a gradation process. The three-dimensional image data obtained by the image processing is displayed in a graphic display unit 120, and is stored in a secondary memory unit 110.

A timing control unit 70 controls the drive signal generating circuit 30 to generate the drive signal at a predetermined timing, and also controls the signal processing unit 61 to accept the detection signal output from the photodetector 16 after the lapse of a predetermined time period from the transmission time of the ultrasonic wave.

Here, three examples will be explained as a two-dimensional sensor array of a photo-detection system.

(1) Example Employing Optical Fiber Array

Figure 2:
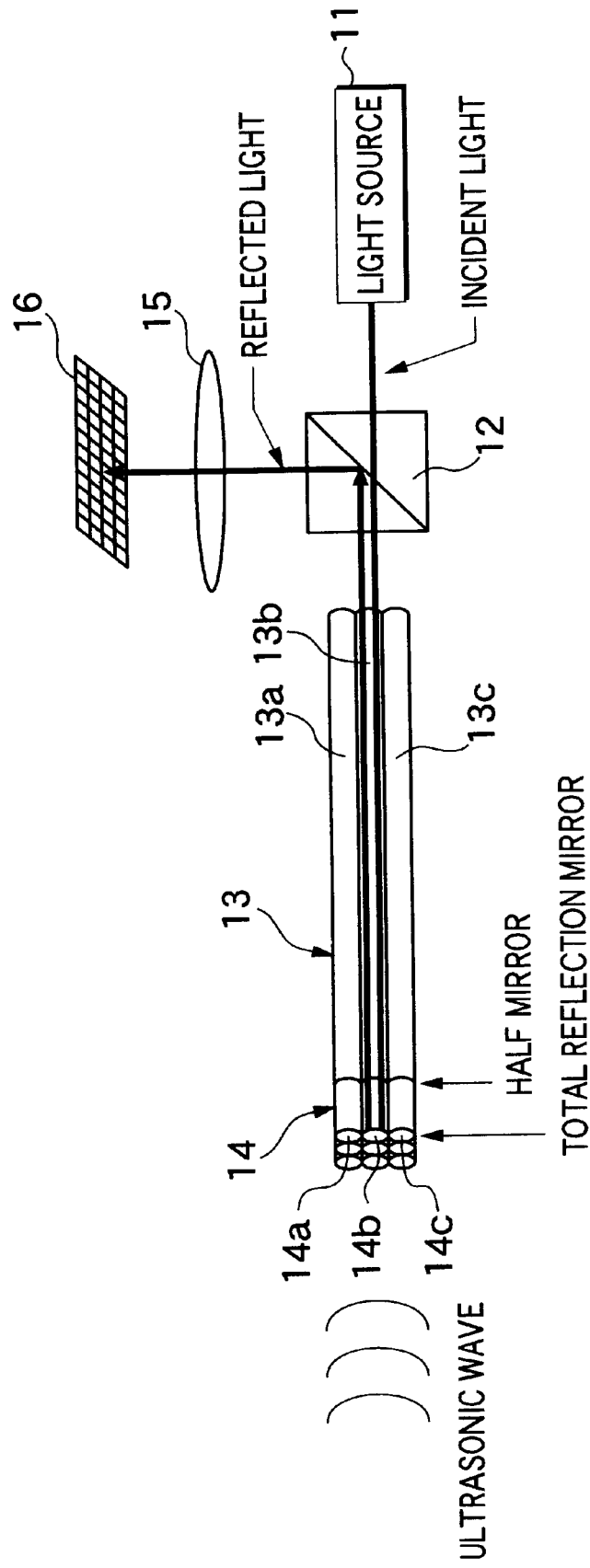
FIG. 2 is a diagram fundamentally showing the first example of an ultrasonic detection unit which can be used in the ultrasonic diagnostic apparatus in FIG. 1.

FIG. 2 is a diagram fundamentally depicting part of the ultrasonic diagnostic apparatus which uses an array of optical fibers each being furnished with an ultrasonic detecting element at its distal end. Referring to FIG. 2, the optical fiber array 13 includes the fine optical fibers 13a, 13b, 13c, . . . whose cross sections are arrayed in the shape of a two-dimensional matrix. Besides, the ultrasonic detecting elements 14 are constructed by, for example, Fabry-Perot resonators (abbreviated to "FPRs") 14a, 14b, 14c, . . . or fiber Bragg gratings which are respectively formed at the distal ends of the individual optical fibers 13a, 13b, 13c, . . . .

Light emitted from the light source 11 passes through the beam separator 12, and enters the optical fiber array 13. A light beam having entered each individual optical fiber is reflected by a half mirror (at the right end of the FPR) and a total reflection mirror (at the left end of the FPR) which are formed at both the ends of the corresponding FPR. Since the total reflection surface undergoes a geometrical displacement by an ultrasonic wave applied to the ultrasonic detecting element 14, the resulting reflected light is thereby modulated, and it enters the beam separator 12 again. The reflected light having entered the beam separator 12 is focussed on the photodetector 16 directly or through an optical fiber or the like, or through the focussing system 15 including a lens etc.

(2) Example Employing Optical-Heterodyne Interferometric Optical System

Figure 3:
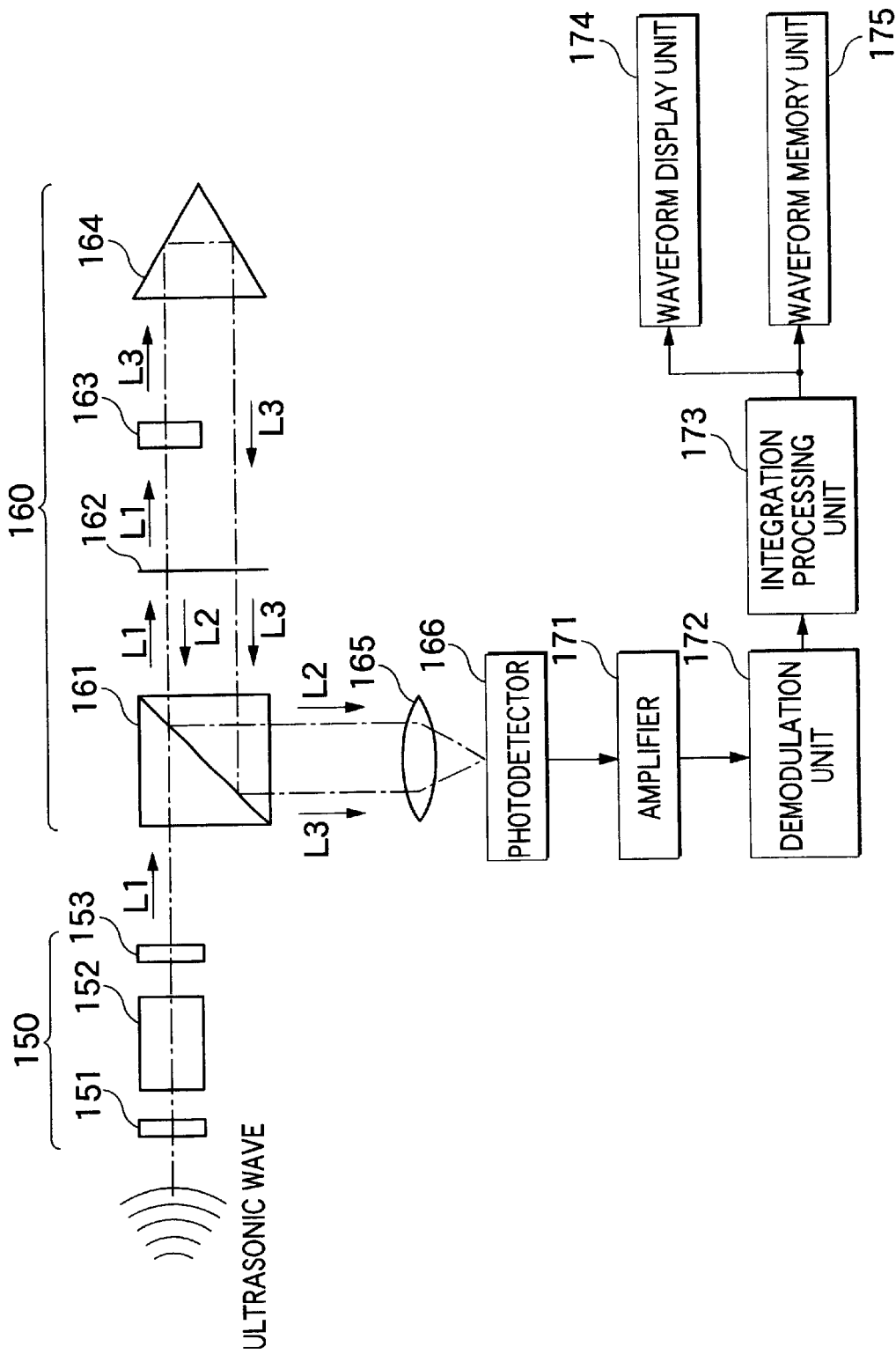
FIG. 3 is a diagram fundamentally showing the second example of the ultrasonic detection unit which can be used in the ultrasonic diagnostic apparatus in FIG. 1.

FIG. 3 is a diagram fundamentally depicting a part of the ultrasonic diagnostic apparatus which includes the two-dimensional sensor array employing an optical-heterodyne interferometric optical system that has an optical path difference. When an ultrasonic wave enters the total reflection mirror 151 of a laser resonator 150, the total reflection mirror 151 is displaced to change the interval between the total reflection mirror 151 and transmission mirror 153 of the laser resonator 150. On this occasion, the oscillation frequency or resonance frequency of a stationary wave which develops between the two mirrors disposed on both the sides of the laser active material 152 of the laser resonator 150 changes, and also the oscillation frequency of the laser deviates. When laser radiation L1 thus emitted enters an interferometric optical system 160, a light beam L2 and a light beam L3 are generated. More specifically, the light beam L2 is generated in such a way that the laser radiation L1 is transmitted through a beam separator 161 and is reflected by a partial reflection mirror 162 as well as the beam separator 161, and it enters a photodetector 166 through a lens 165. On the other hand, the light beam L3 is generated in such a way that the laser radiation L1 is transmitted through the beam separator 161 as well as the partial reflection mirror 162, is passed through a frequency shifter 163 as well as a prism 164, is transmitted through the partial reflection mirror 162 again and is reflected by the beam separator 161, and it enters the photodetector 166 through the lens 165. An optical path difference arises between the light beams L2 and L3.

Here, when the light beam whose oscillation frequency deviates temporally enters the optical-heterodyne interferometric optical system having the optical path difference, a beat signal is generated at a frequency which shifts by the variation of an oscillation frequency corresponding to a time delay component from a frequency of the original optical-heterodyne interference signal. The frequency-modulated beat signal is amplified by an amplifier 171 and is demodulated by a demodulation unit 172, and the resulting demodulated signal is integrated and processed by an integration processing unit 173. Then, the change of the frequency, that is, the waveform of the ultrasonic wave can be reproduced. This waveform is displayed on a waveform display unit 174, and is simultaneously stored in a waveform memory unit 175.

(3) Example Employing Evanescent Field

Figure 4:
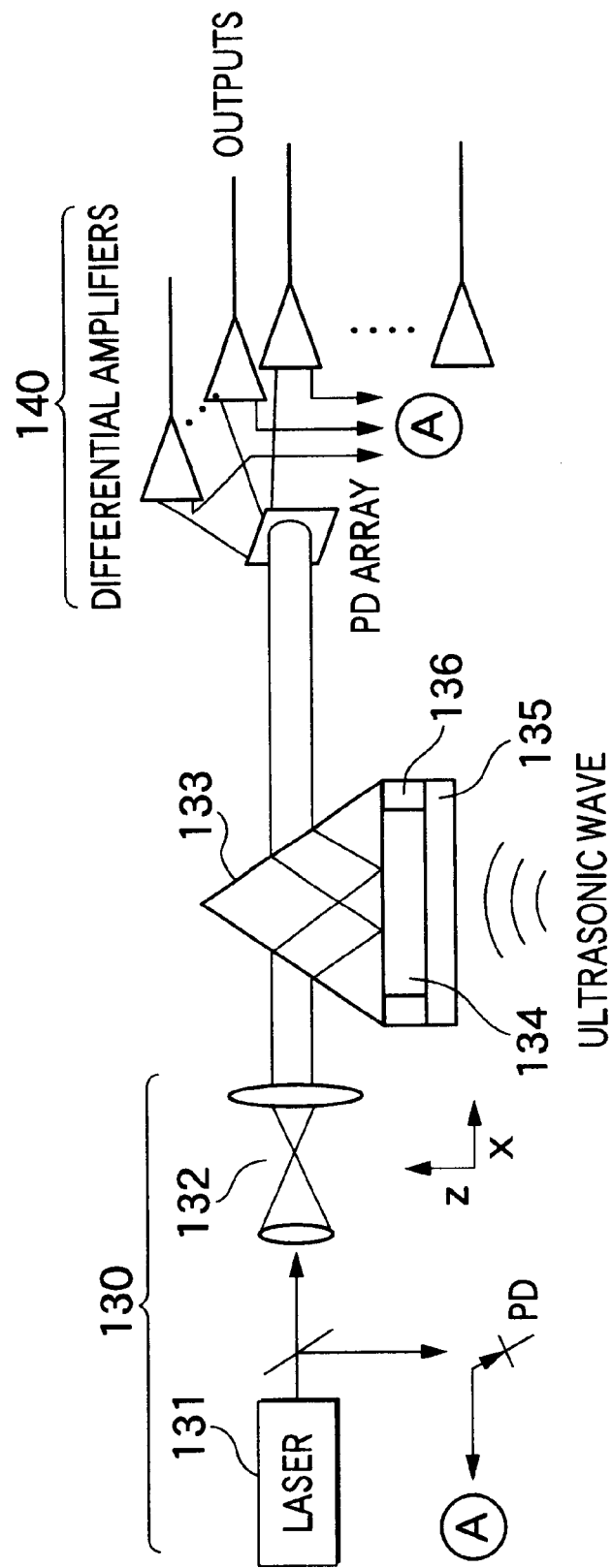
FIG. 4 is a diagram fundamentally showing the third example of the ultrasonic detection unit which can be used in the ultrasonic diagnostic apparatus in FIG. 1.

FIG. 4 is a diagram fundamentally depicting part of the ultrasonic diagnostic apparatus which includes an ultrasonic transducer utilizing the phenomenon that an object existing in an evanescent field vicinal to a reflection interface is oscillated by receiving an ultrasonic wave whereby the quantity of evanescent light changes. Referring to FIG. 4, the ultrasonic transducer is constituted by a prism 133, a gap portion 134, an optical flat 135 and a spacer 136 for defining a gap. When an ultrasonic wave enters the transducer from the lower surface of the optical flat 135, the quantity of total reflection light at the bottom of the prism 133 changes depending upon the acoustic pressure level of the ultrasonic wave. Accordingly, the spatial distribution and temporal change of the ultrasonic wave can be measured in such a way that the prism bottom is illuminated with an expanded laser beam which is emitted from a light source 130 constituted by a laser resonator 131 and a beam expander 132, and that the intensity distribution of the total reflection light is read by a photodetector 140.

Next, the operation of the ultrasonic diagnostic apparatus to which the image data computing apparatus according to the first embodiment of the present invention is applied will be described in detail with reference to FIGS. 1 and 5.

Figure 5:
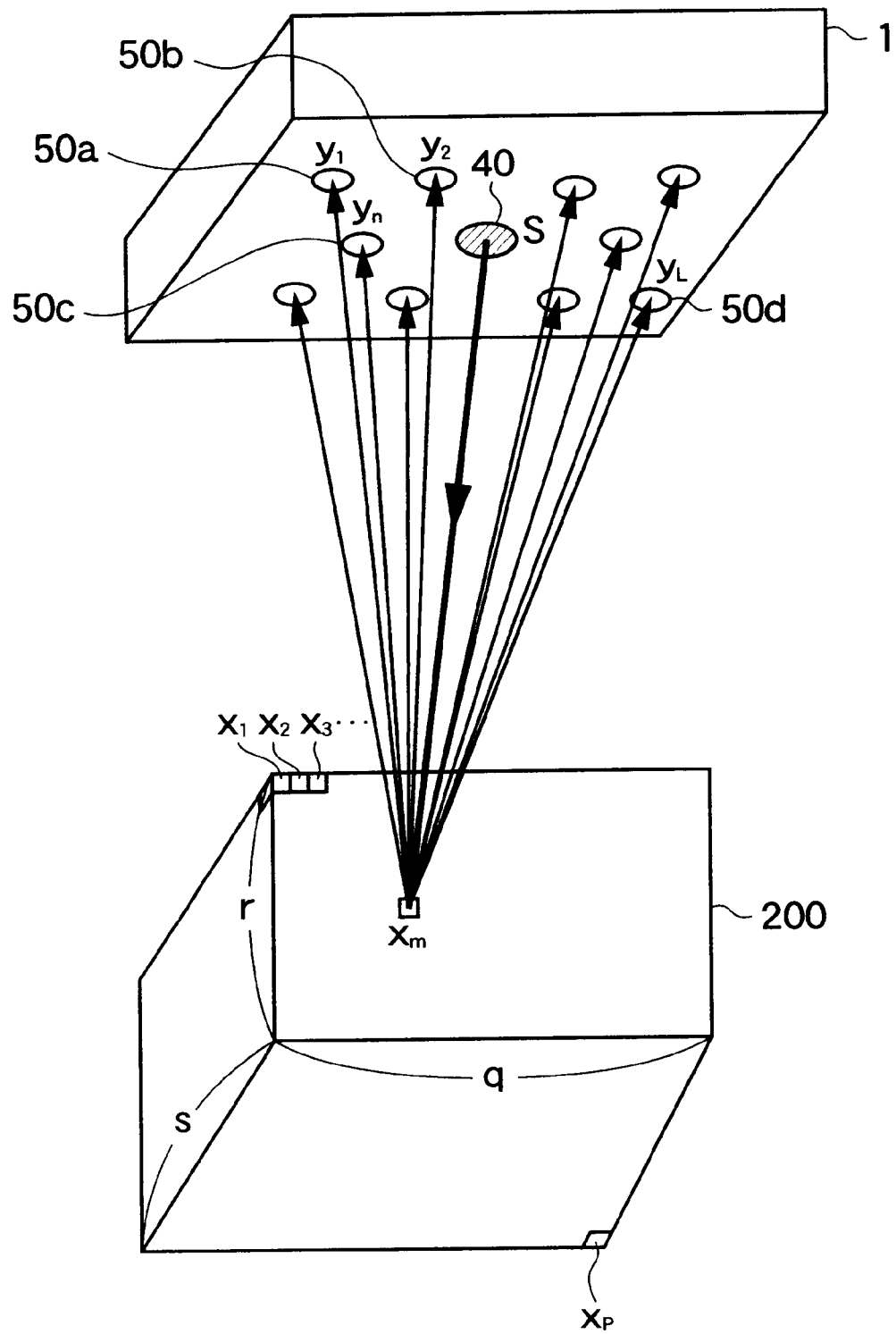
FIG. 5 is a diagram showing the travelling paths of a directional ultrasonic beam which is transmitted from an ultrasonic transmission unit.

FIG. 5 is a diagram showing the travelling paths of an ultrasonic beam which is transmitted from the ultrasonic transmission unit. In this embodiment, the ultrasonic beam which is transmitted from the ultrasonic transmission unit will be explained as being directional. Shown in FIG. 5 are a part of the ultrasonic transmitting and receiving unit (probe) 1, and an object 200 which includes P points to be measured (P=q×r×s). The ultrasonic transmitting and receiving unit (probe) 1 includes the ultrasonic transmission unit 40 and a plurality of ultrasonic detecting elements (sensors) 50a, 50b, . . . constituting the ultrasonic detection unit 50. A reference mark "S" as shown in FIG. 5 denotes a position of the ultrasonic transmission unit 40, and reference marks "$y_1$, $y_2$, . . . $y_n$, . . . , $y_L$" denote positions of the respective sensors 50a, 50b, . . . . Besides, reference marks "$x_1, x_2, \ldots, x_m, \ldots, x_P$" denote positions of the respective points to be measured which are included in the object 200.

Referring to FIG. 5, the directional ultrasonic beam transmitted from the ultrasonic transmission unit 40 is reflected at one point to be measured "$x_m$" and is detected by the L sensors 50a, 50b, . . . being non-directional. The detected ultrasonic wave components are converted into light intensity signals in the ultrasonic detection unit 50.

Here, reference will be made to FIG. 6 which is a block diagram showing the connection of the line memory.

Figure 6:
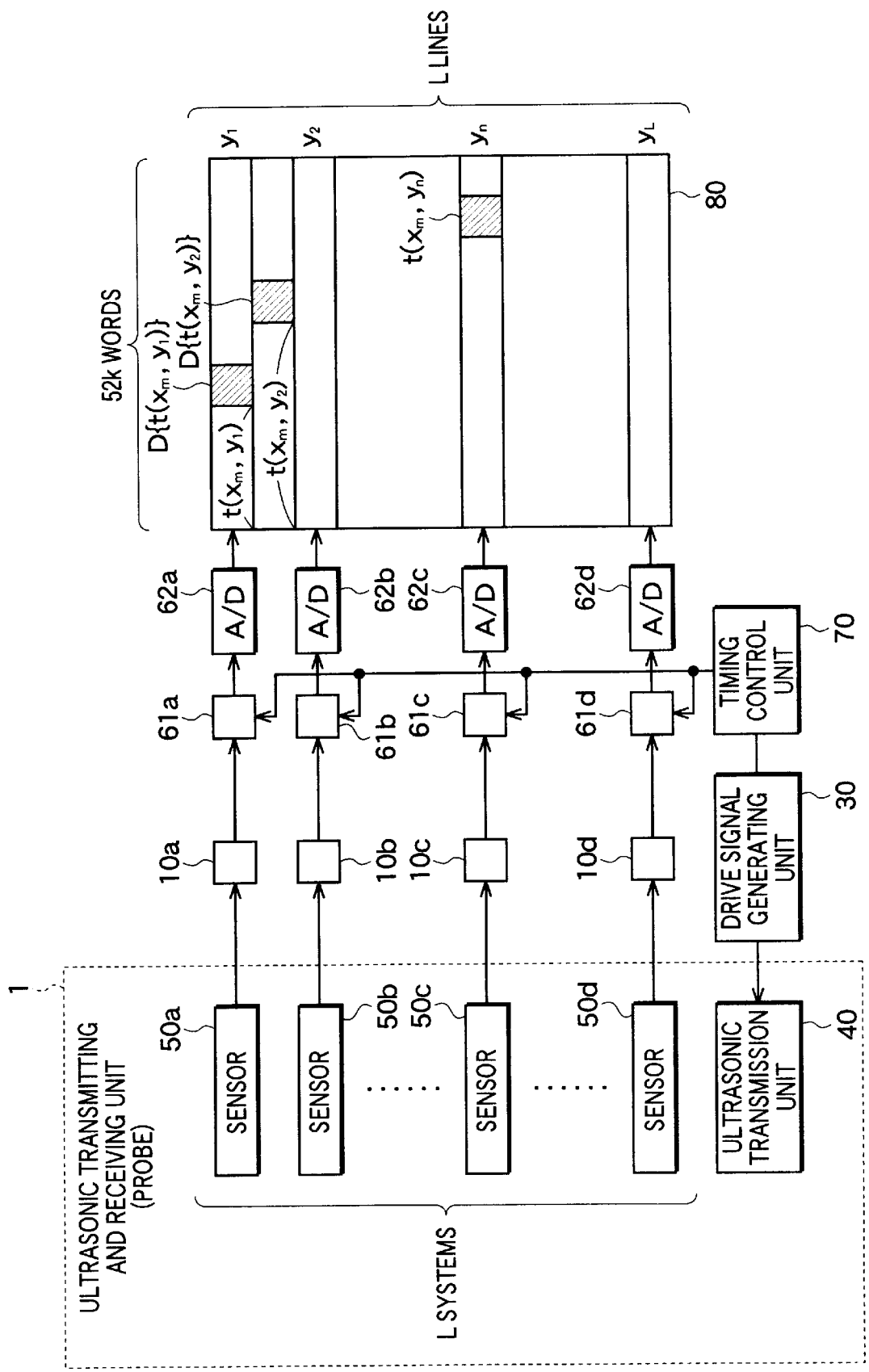
FIG. 6 is a diagram showing connection of a line memory in the image data computing apparatus according to the first embodiment of the present invention.

Referring to FIG. 6, optical systems 10a, 10b, . . . are connected to the sensors 50a, 50b, . . . , respectively. The detection signals output from the optical systems 10a, 10b, . . . are processed by signal processing units 61a, 61b, . . . and then converted into detection data in A/D converters 62a, 62b, . . . , respectively. Each of the optical systems 10a, 10b, . . . may well include the beam separator 12, focussing system 15 and photodetector 16 which are shown in FIG. 1. Besides, the timing control unit 70 controls the ultrasonic transmission unit 40 and the signal processing units 61a, 61b, . . . .

The line memory 80 has L lines which correspond to the L sensors. The number of words to be possessed by each of the lines can be determined from the thickness and size of the object to be inspected. More specifically, into each line of the line memory 80, detection data obtained by the corresponding sensor are input in time series. Assuming by way of example that the thickness of the human body is 20 cm or so, a time period which is required for an ultrasonic wave to pass through the human body in both ways is about 260 μsec. It is accordingly allowed to prepare a storage capacity enough to store samples which are obtained during 260 μsec since the time point of the transmission of the ultrasonic wave. Here, in a case where one sample is formed of data of one word and where data are acquired at a rate of 200 M (mega) samples per second, the storage capacity which is required for each line of the memory 80 becomes:

200 M samples/sec×260 μsec=52 k words

Referring to FIG. 5 again, the ultrasonic wave transmitted from the ultrasonic transmission unit 40 travels via the point to be measured "$x_m$" and is detected by the sensor 50a located at the position "$y_1$". Referring to FIG. 6, the timing control unit 70 outputs a data acceptance signal after the lapse of a predetermined time period from the time of the transmission of the ultrasonic wave. Then, light intensity signals having entered the optical system 10a within the predetermined time period are accepted into the signal processing unit 61a as electric signals, which are converted by the A/D converter 62a. Further, the detection data produced by the A/D conversion are input to the line "$y_1$" of the line memory 80. The detection data thus acquired through the detection by the sensor 50a and the A/D conversion by the A/D converter 62a are accumulated in the line "$y_1$" of the line memory 80 in time series. Similar operations proceed as to the other sensors, and signals detected by the sensor 50c located at the position "$y_n$" (FIG. 5) are input to the line "$y_n$" of the line memory 80 via the optical system 10c connected with this sensor 50c, signal processing unit 61c and A/D converter 62c.

In this manner, the detection data concerning the points to be measured "$x_m$" etc., that is, the detection data $D(y_1)$ detected by the sensor 50a to the detection data $D(y_L)$ detected by the sensor 50d are stored in the respective lines "$y_1$" to "$y_L$" of the line memory 80.

FIG. 7 shows the format of the table 100 where are stored transfer time period data, etc. to be used in computing image data on the basis of the detection data stored in the line memory 80. As shown in FIG. 7, the table 100 has P lines which correspond to the P points to be measured "$x_1, x_2, \ldots, x_m, \ldots, x_P$" included in the object 200, and L columns which correspond to the positions "$y_1, y_2, \ldots, y_n, \ldots, y_L$" of the L sensors. Here, $1 \leq m \leq P$ and $1 \leq n \leq L$ hold.

Referring back to FIG. 5, a time period $t(x_m, y_1)$ after which the ultrasonic wave is detected by the sensor 50a from its transmission is expressed by using the position "S" of the ultrasonic transmission unit 40, the position "$x_m$" of a certain point to be measured and a position "$y_1$" of the sensor 50a, as follows:

$t(x_m, y_1)$=(Distance along "S" to "$x_m$" to "$y_1$")/(Velocity of ultrasonic wave)

That is, the signal detected by the sensor 50a at the position "$y_1$" after a time period $t(x_m, y_1)$ from the transmission of the ultrasonic beam is decided as concerning the point to be measured "$x_m$". Likewise, the signal detected by the sensor 50c at the position "$y_n$" after a time period $t(x_m, y_n)$ from the transmission of the ultrasonic beam is decided as concerning the point to be measured "$x_m$".

Transfer time period data $t(x_m, y_n)$ expressive of the time period which is required for the sensor 50c at the position "$y_n$" to detect the data concerning the point to be measured "$x_m$" from the transmission of the ultrasonic beam, is stored in line "m" and column "n" of the table 100. Likewise, as to the other sensors, transfer time period data are stored in the corresponding lines and columns of the table 100. Accordingly, detection data concerning the point to be measured "$x_m$" can be selected from among the detection data stored in the line memory 80, by referring to the transfer time period data $t(x_m, y_1), t(x_m, y_2), \ldots, t(x_m, y_n), \ldots, t(x_m, y_L)$ which are stored in the "m"th line of the table 100.

Since the transfer time period data are determined by the mutual positional relations between the sensors 50a, 50b, ... and the points to be measured "$x_1, x_2, \ldots$", the transfer time period data concerning the P points to be measured as correspond to each of the L sensors are input to the table 100 beforehand.

Here, the transfer time period data may be expressed by a time point which has been measured from a time point of the transmission of the ultrasonic beam. Alternatively, the transfer time period data may well be expressed by a difference $\Delta t(x_m, y_n)$ from a reference time period "$t_0$". In this case, $t(x_m, y_n)$ is obtained as follows:

$t(x_m, y_n) = t_0 + \Delta t(x_m, y_n)$

Usable as the reference time period is, for example, a time period which is required for the sensor, which has the shortest distance from the point to be measured, to detect the signal from the time point of the transmission of the ultrasonic beam.

The image processing unit 90 as shown in FIG. 1 computes the image data of each point to be measured by reference to the table 100 on the basis of the detection data stored in the line memory 80. More specifically, the image data "$D_m$" concerning the point to be measured "$x_m$" is computed by superposing the detection data which correspond to the transfer time period data $t(x_m, y_1), t(x_m, y_2), \ldots, t(x_m, y_L)$ input to the "m"th line, as follows:

$$D_m = D\{t(x_m, y_1), y_1\} + D\{t(x_m, y_2), y_2\} + \ldots + D\{t(x_m, y_L), y_L\} \qquad (1)$$

$$= \sum_{n=1}^{L} D\{t(x_m, y_n), y_n\}$$

Likewise, the image processing unit 90 computes the image data as to the other points to be measured "$x_1$" to "$x_P$".

The image processing unit 90 composes three-dimensional image data on the basis of these image data. The composed three-dimensional image data is further subjected to processes, such as an interpolation process, a response modulation process and a gradation process, and is displayed on the graphic display unit 120. Besides, the data processed in the image processing unit 90 is stored in the secondary memory unit 110 so as to be output at need.

Next, an image data computing apparatus according to the second embodiment of the present invention will be described. The image data computing apparatus according to this embodiment is such that weighting factors which weight image data in computing the data within the image processing unit 90 are placed in the table 100.

Figure 8:
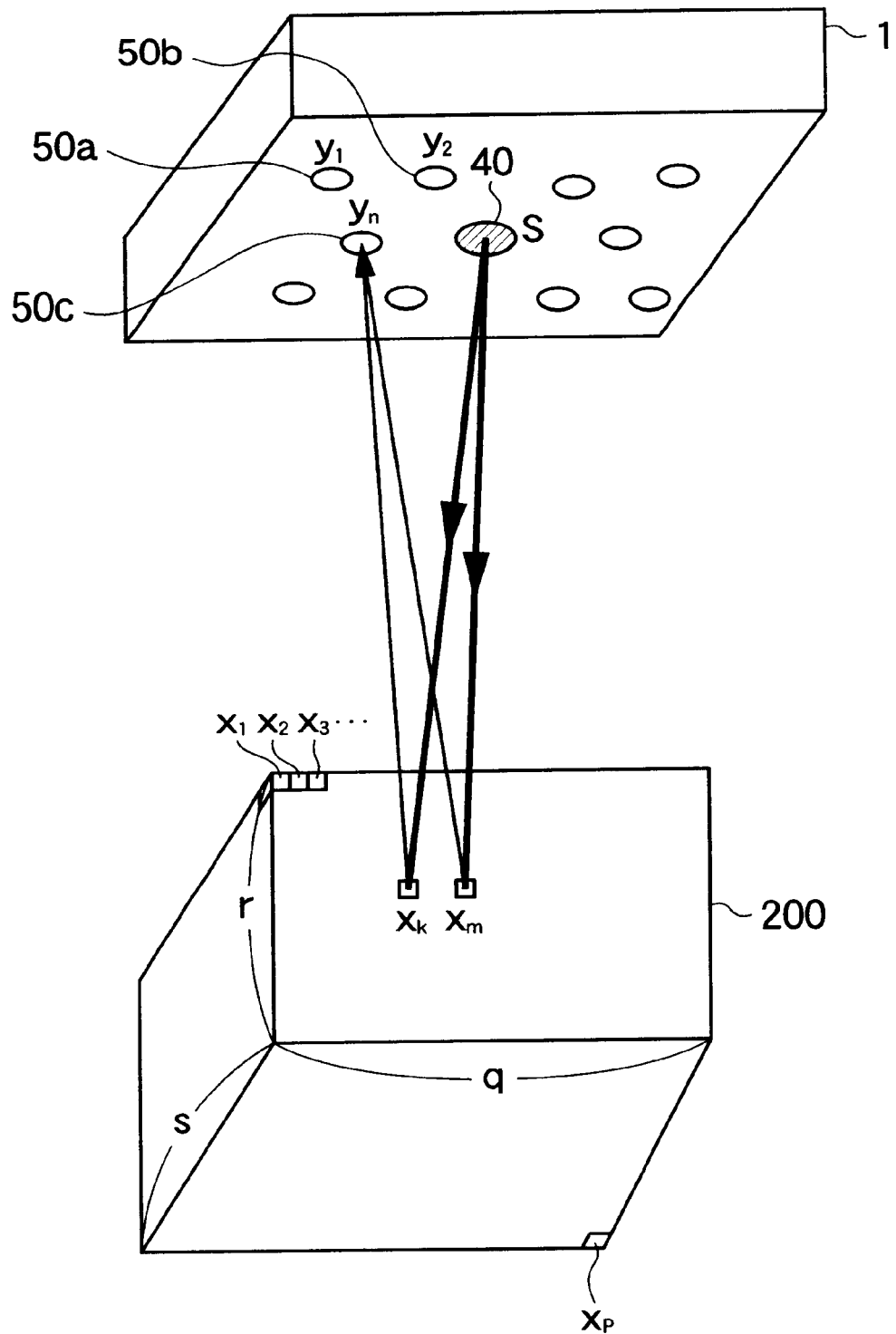
FIG. 8 is a diagram showing the travelling paths of a non-directional ultrasonic beam which is transmitted from the ultrasonic transmission unit.

In a case, for example, where the quantity of attenuation of the ultrasonic wave as corresponds to each distance extending along the transmission point "S" to each sensor via the point to be measured "x" is desired to be corrected, or in a case where the data are desired to be thinned out, the respective data values may be weighted and then added in computing the image data. Meanwhile, as shown in FIG. 8, in a case where an ultrasonic wave which is transmitted by the ultrasonic transmission unit 40 is non-directional, signals concerning those points to be measured "$x_k$" and "$x_m$" of different positions which have equal distances extending along the ultrasonic transmission point "S" to the sensor position "$y_n$" via the point to be measured are concurrently detected by the sensor 50c located at the position "$y_n$". In other words, the data value $D\{t(x_k, y_n), y_n\}$ is contained in the data value $D\{t(x_m, y_n), y_n\}$. In such a case, it is desirable that the influence of the data from the different point is made relatively little by increasing the number of constituents in the addition, while at the same time, necessary weights are afforded to the data values in the respective sensors.

FIG. 9 shows the format of the table 100 where are stored transfer time period data, weighting factors, etc. to be used in computing image data on the basis of the detection data stored in the line memory 80. As shown in FIG. 9, the table 100 has 2P lines which correspond to P transfer time period data and P weighting factors to multiply the respective detection data values, as to the P points to be measured "$x_1, x_2, \ldots, x_m, \ldots, x_P$" included in the object 200, and L columns which correspond to the positions "$y_1, y_2, \ldots, y_n, \ldots, y_L$" of the L sensors. Here, $1 \leq m \leq P$ and $1 \leq n \leq L$ hold.

Referring to FIG. 9, $W(x_m, y_n)$ denotes the weighting factor which multiplies detection data $D\{t(x_m, y_n), y_n\}$ detected at the time point $t(x_m, y_n)$ by the sensor located at the position "$y_n$". The weighting factors may well be set so as to take either one of only the two values of zero and a predetermined number. By way of example, the weighting factors are set at "0" and "1", whereby the detection data can be thinned out.

The image processing unit 90 computes the image data of each point to be measured by reference to the table 100 on the basis of the detection data stored in the line memory 80. More specifically, the image data "$D_m$" concerning the point to be measured "$x_m$" is computed using the detection data which correspond to the time points $t(x_m, y_1), t(x_m, y_2), \ldots, t(x_m, y_L)$, and the weighting factors $W(x_m, y_1), W(x_m, y_2), \ldots, W(x_m, y_L)$, as follows:

$$D_m = W(x_m, y_1) \times D\{t(x_m, y_1), y_1\} + \quad (2)$$
$$W(x_m, y_2) \times D\{t(x_m, y_2), y_2\} + \ldots +$$
$$W(x_m, y_L) \times D\{t(x_m, y_L), y_L\}$$
$$= \sum_{n=1}^{L} W(x_m, y_n) \times D\{t(X_m, y_n), y_n)\}$$

On the basis of these image data, three-dimensional image data is composed in the image processing unit 90. The composed three-dimensional image data is further subjected to image processes such as an interpolation process, a response modulation process and a gradation process, and it is displayed on the graphic display unit 120 and is stored in the secondary memory unit 110.

According to this embodiment, the detected data values are appropriately weighted and are used for computing the image data, so that the image data of good quality at a high S/N ratio can be obtained.

Figure 10:
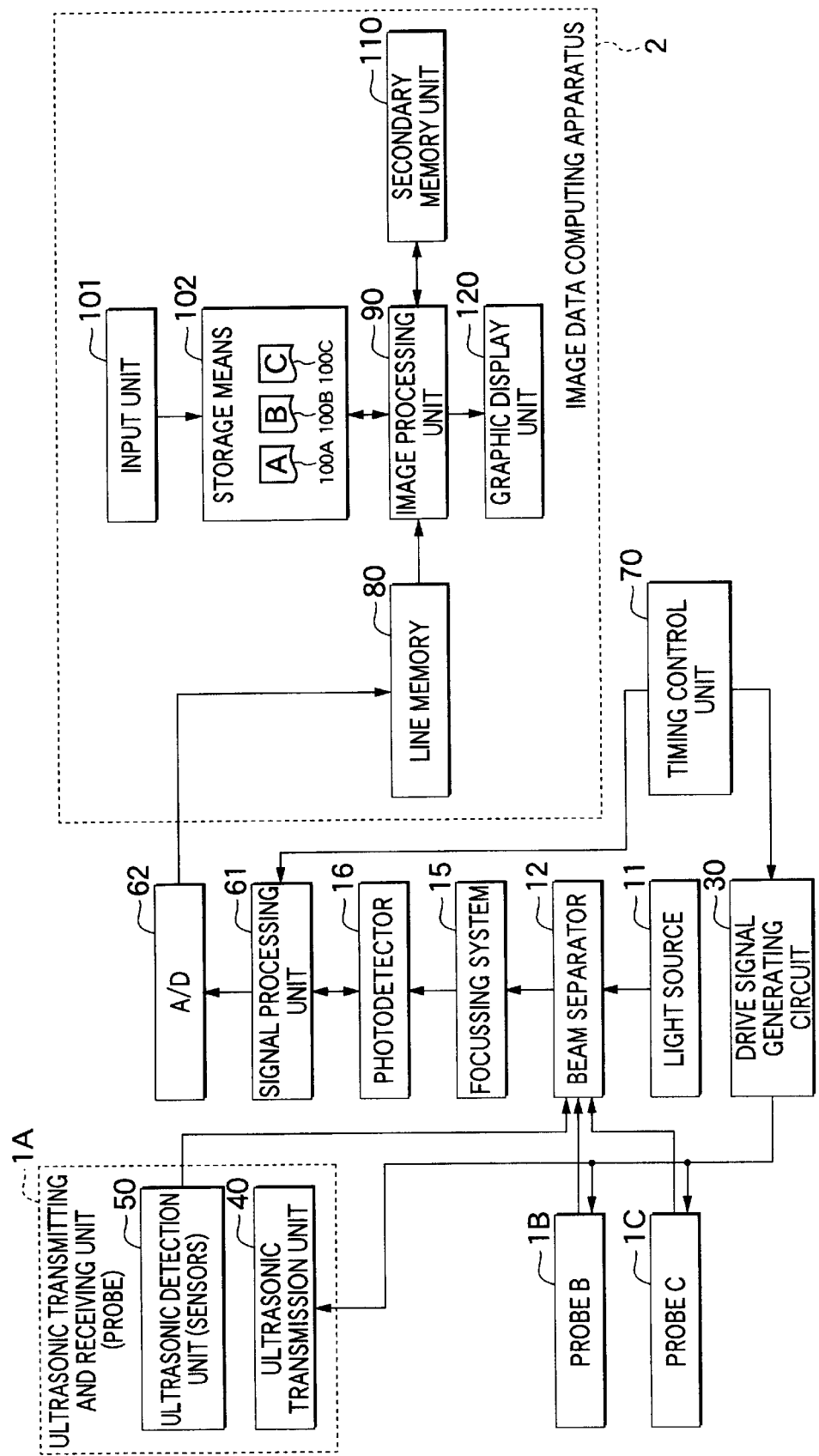
FIG. 10 is a block diagram showing an ultrasonic diagnostic apparatus which includes an image data computing apparatus according to the third embodiment of the present invention.

Next, an image data computing apparatus according to the third embodiment of the present invention will be described. FIG. 10 is a block diagram showing an ultrasonic diagnostic apparatus which includes the image data computing apparatus according to this embodiment. Referring to FIG. 10, the ultrasonic diagnostic apparatus has a plurality of probes which are ultrasonic transmitting and receiving units. In ultrasonic diagnoses, probes which differ in shape, size, the number of sensors, etc. are used depending upon the parts of objects to be photographed. In this embodiment, therefore, the plurality of probes are connected to a main body of the single ultrasonic diagnostic apparatus so as to be adapted for various objects.

As shown in FIG. 10, each of the probes 1A, 1B and 1C is connected to the main body of the image data computing apparatus through a beam separator 12 or a drive signal generating circuit 30. Besides, storage means 102 such as a memory or a recording device stores tables 100A, 100B and 100C as attendant information, which are respectively associated with the corresponding probes. The numbers of lines and columns contained in each of the tables 100A, 100B and 100C are determined by the number of sensors included in the corresponding probe and the sizes of the intended objects to be photographed. Besides, each table may well contain weighting factors which correspond to the objects to be photographed.

The table for use in computing image data may well be determined in such a way that the tables corresponding to the plurality of probes have been stored in the main body of the apparatus beforehand, and that any of the stored tables is externally selected through an input unit 101 when computing the image data. Alternatively, the table corresponding to the probe may well be automatically selected when the particular probe is used.

Figure 11:
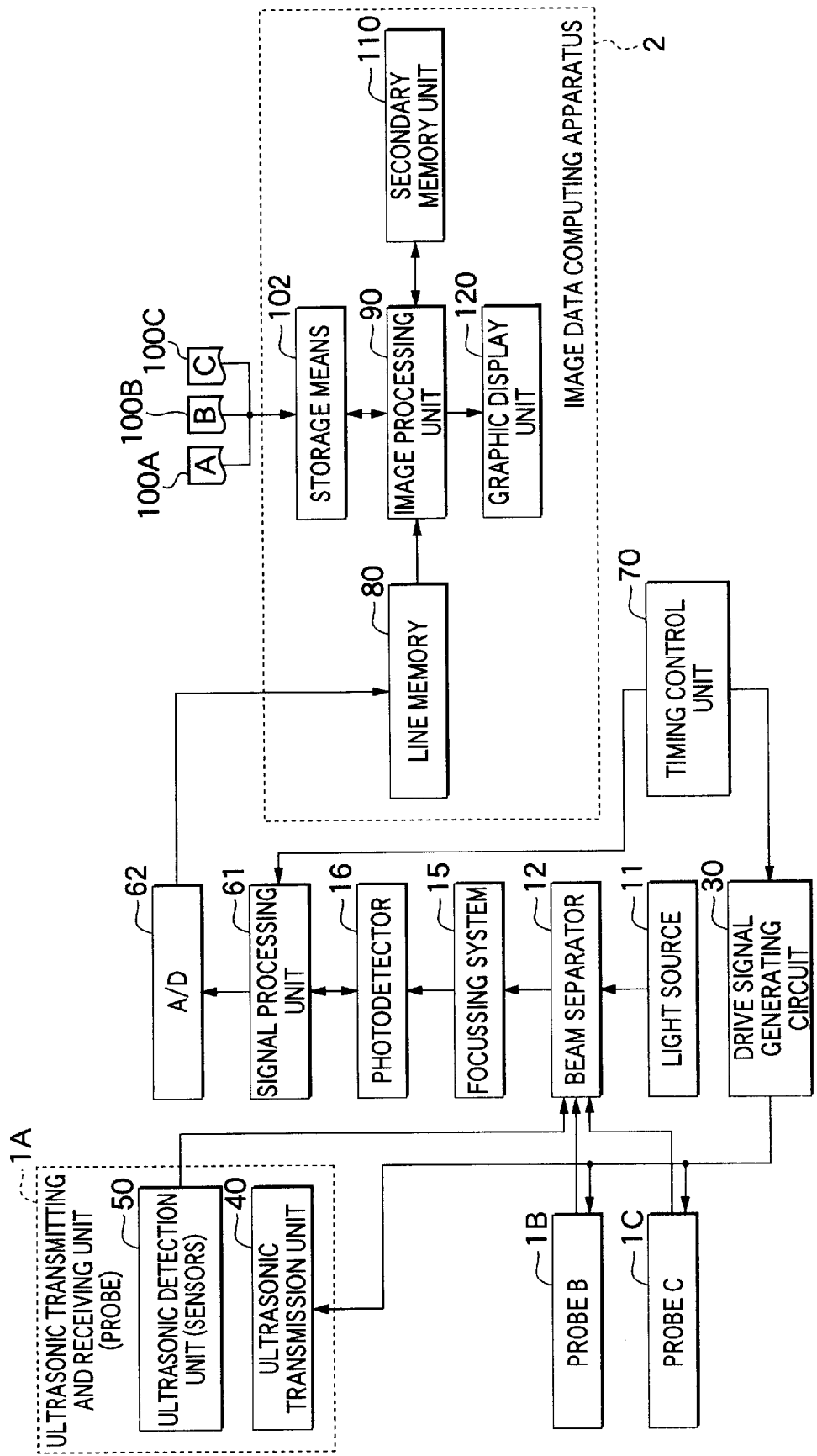
FIG. 11 is a block diagram showing a modification to the third embodiment of the present invention.

Further, as shown in FIG. 11, the data files of the tables 100A to 100C respectively corresponding to the probes 1A to 1C may well be stored in a recording medium, for example, floppy disk so as to load the necessary data file and then store it into the storage means 102 when computing the image data.

Figure 12:
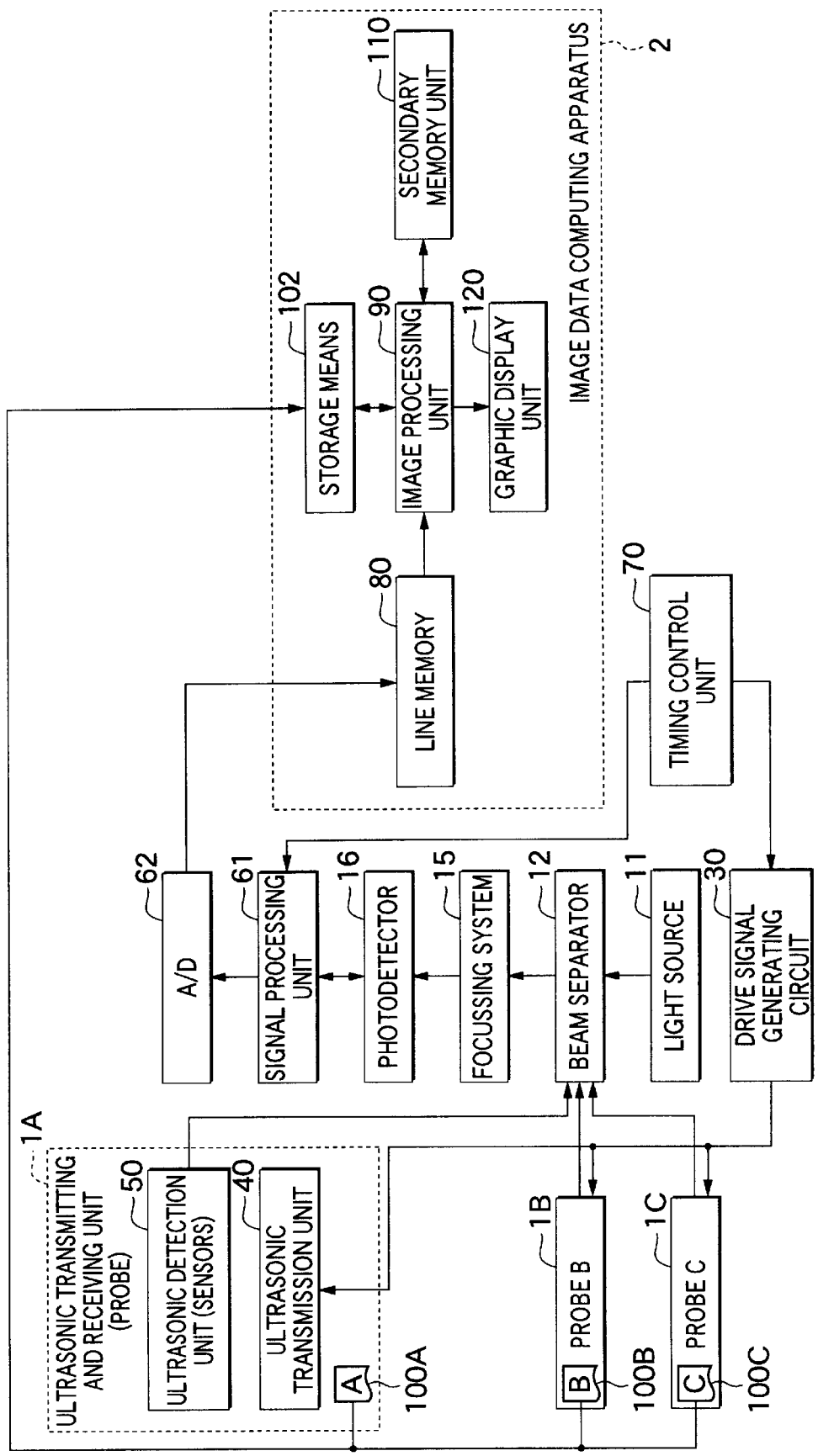
FIG. 12 is a block diagram showing another modification to the third embodiment of the present invention.

Alternatively, as shown in FIG. 12, the probes 1A to 1C may well include memories in which the data of the tables 100A–100C corresponding to the respective probes are stored, so that the necessary data is automatically loaded and then stored into the storage means 102 when starting the use of the particular probe.

As described above, according to the present invention, three-dimensional image data can be computed on the basis of a plurality of two-dimensional image data acquired at identical array positions at different times by employing a two-dimensional sensor array. Accordingly, a clear three-dimensional image can be obtained even in an ultrasonic diagnostic apparatus which is directed toward organisms.

What is claimed is:

1. An image data computing apparatus for computing three-dimensional image data on the basis of detection data obtained by transmitting an ultrasonic wave from transmission means toward points to be measured, which exist in a three-dimensional space, and detecting the ultrasonic wave reflected from the points to be measured by use of a two-dimensional sensor array including a plurality of sensors, said apparatus comprising:

a line memory having a plurality of lines for storing the detection data obtained on the basis of output signals of said plurality of sensors respectively for a predetermined time period;

storage means for storing as a table therein transfer time period data determined by relations between distances from the transmission means to the respective sensors through the respective points to be measured and transfer velocities of the ultrasonic wave in corresponding paths; and computation means for reading the detection data stored in said line memory in accordance with the transfer time period data stored in said storage means for the respective points to be measured, and for computing image data at the respective points to be measured on the basis of the read detection data.

2. An image data computing apparatus according to claim 1, wherein said storage means stores a plurality of tables.

3. An image data computing apparatus according to claim 1, further comprising a plurality of probes each includes the two-dimensional sensor array, wherein said storage means stores a plurality of tables which correspond to said plurality of probes, respectively.

4. An image data computing apparatus according to claim 3, wherein said plurality of tables respectively corresponding to said plurality of probes have been stored in a main body of said image data computing apparatus as data to be used in correspondence with said plurality of probes, respectively.

5. An image data computing apparatus according to claim 3, wherein said plurality of tables respectively corresponding to said plurality of probes are stored into a main body of said image data computing apparatus through recording media to be handled in correspondence with said plurality of probes, respectively.

6. An image data computing apparatus according to claim 3, wherein said plurality of tables respectively corresponding to said plurality of probes are stored in said plurality of probes, respectively.

7. An image data computing apparatus according to claim 1, wherein each of the transfer time period data determined by the relations between the distances from the transmission means to the respective sensors through the respective points to be measured and transfer velocities of the ultrasonic wave in the corresponding paths is expressed by a reference time and a difference from the reference time.

8. An image data computing apparatus according to claim 1, further comprising:

a plurality of detection signal processing means which correspond to said plurality of sensors, respectively; and a plurality of A/D converters for converting detection signals, which are output from said plurality of detection signal processing means, into the detection data to supply the detection data to said line memory having the plurality of lines, respectively.

9. An image data computing apparatus for computing three-dimensional image data on the basis of detection data obtained by transmitting an ultrasonic wave from transmission means toward points to be measured, which exist in a three-dimensional space, and detecting the ultrasonic wave reflected from the points to be measured by use of a two-dimensional sensor array including a plurality of sensors, said apparatus comprising:

a line memory having a plurality of lines for storing the detection data obtained on the basis of output signals of said plurality of sensors respectively for a predetermined time period;

storage means for storing as a table therein transfer time period data determined by relations between distances from the transmission means to the respective sensors through the respective points to be measured and transfer velocities of the ultrasonic wave in corresponding paths, and weighting factors for the detection data; and computation means for reading the detection data stored in said line memory in accordance with the transfer time period data stored in said storage means for the respective points to be measured, and for computing image data at the respective points to be measured by adding the read detection data after multiplying them by the weighting factors stored in said storage means for the respective points to be measured.

10. An image data computing apparatus according to claim 9, wherein each of the weighting factors takes either one of zero and a predetermined number.

11. An image data computing apparatus according to claim 9, wherein said storage means stores a plurality of tables.

12. An image data computing apparatus according to claim 9, further comprising a plurality of probes each includes the two-dimensional sensor array, wherein said storage means stores a plurality of tables which correspond to said plurality of probes, respectively.

13. An image data computing apparatus according to claim 12, wherein said plurality of tables respectively corresponding to said plurality of probes have been stored in a main body of said image data computing apparatus as data to be used in correspondence with said plurality of probes, respectively.

14. An image data computing apparatus according to claim 12, wherein said plurality of tables respectively corresponding to said plurality of probes are stored into a main body of said image data computing apparatus through recording media to be handled in correspondence with said plurality of probes, respectively.

15. An image data computing apparatus according to claim 12, wherein said plurality of tables respectively corresponding to said plurality of probes are stored in said plurality of probes, respectively.

16. An image data computing apparatus according to claim 9, wherein each of the transfer time period data determined by the relations between the distances from the transmission means to the respective sensors through the respective points to be measured and transfer velocities of the ultrasonic wave in the corresponding paths is expressed by a reference time and a difference from the reference time.

17. An image data computing apparatus according to claim 9, further comprising:

a plurality of detection signal processing means which correspond to said plurality of sensors, respectively; and a plurality of A/D converters for converting detection signals, which are output from said plurality of detection signal processing means, into the detection data to supply the detection data to said line memory having the plurality of lines.

18. An image data computing apparatus according to claim 9, wherein said computation means is operative to correct a quantity of attenuation of the ultrasonic wave according to each distance extending along a transmission point to each sensor in said plurality of sensors via the point to be measured.

19. An image data computing apparatus according to claim 9, wherein said computation means is operative to apply said weighting factors where the data is desired to be thinned out.

20. An image data computing apparatus according to claim 9, wherein said computation means is operative to apply said weighting factors where an ultrasonic wave, which is transmitted from the ultrasonic transmission unit is non-directional.

* * * * *